United States Patent [19]

Kamen

[11] Patent Number: 4,976,162
[45] Date of Patent: Dec. 11, 1990

[54] ENHANCED PRESSURE MEASUREMENT FLOW CONTROL SYSTEM

[76] Inventor: Dean L. Kamen, 44 Gage Rd., Bedford, N.H. 03102

[21] Appl. No.: 345,387

[22] Filed: May 1, 1989

Related U.S. Application Data

[63] Continuation-in-part of Ser. No. 92,481, Sep. 3, 1987, Pat. No. 4,826,482, which is a continuation-in-part of Ser. No. 22,167, Mar. 5, 1987, Pat. No. 4,808,161, which is a continuation-in-part of Ser. No. 836,023, Mar. 4, 1986, Pat. No. 4,778,451.

[51] Int. Cl.[5] .............................................. G01F 17/00
[52] U.S. Cl. .................................... 73/865.9; 73/149; 364/564
[58] Field of Search ................... 73/149, 865.9, 290 B; 364/564

[56] References Cited

U.S. PATENT DOCUMENTS

| | | | |
|---|---|---|---|
| 2,166,636 | 5/1938 | Neumann | 73/290 |
| 2,747,400 | 5/1956 | Fatio | 73/149 |
| 4,227,420 | 10/1980 | Lamadrid | 73/756 |
| 4,479,760 | 10/1984 | Bilstad et al. | 417/395 |
| 4,479,761 | 10/1984 | Bilstad et al. | 417/395 |
| 4,479,762 | 10/1984 | Bilstad et al. | 417/395 |
| 4,486,190 | 12/1984 | Reinicke | 604/67 |
| 4,561,298 | 12/1985 | Pond | 73/149 |
| 4,634,430 | 1/1987 | Polaschegg | 604/141 |
| 4,781,061 | 11/1988 | Baumgartl | 73/149 |
| 4,833,922 | 5/1989 | Frick et al. | 73/756 |

FOREIGN PATENT DOCUMENTS

| | | |
|---|---|---|
| 0156211 | 10/1985 | European Pat. Off. . |
| 2110349 | 6/1972 | France . |
| 8404460 | 11/1984 | PCT Int'l Appl. . |

Primary Examiner—Jerry W. Myracle
Attorney, Agent, or Firm—Bromberg & Sunstein

[57] ABSTRACT

A system for measuring flow of fluid through a line. A portion of the fluid in the line is isolated in a rigid container so that the fluid in the container is not affected by pressure in the rest of the line. An apparatus is provided for measuring that portion of the container that is not occupied by the fluid. In order to urge fluid into and out of the container, a positive pressure source, for providing gas to the container, and a negative pressure source for removing gas from the container, are provided for.

8 Claims, 8 Drawing Sheets

ENHANCED PRESSURE MEASUREMENT FLOW CONTROL SYSTEM

CROSS-REFERENCE TO RELATED APPLICATIONS

This is a continuation-in-part of application Ser. No. 092,481, filed on Sept. 3, 1987, now U.S. Pat. No. 4,826,482 which is a continuation-in-part of applications Ser. No. 022,167, filed Mar. 5, 1987, issued as U.S. Pat. No. 4,808,161 on Feb. 28, 1987, and of application No. 836,023, filed on Mar. 4, 1986 now U.S. Pat. No. 4,778,451. These related applications are hereby incorporated herein by reference.

BACKGROUND OF THE INVENTION

1. Field of Invention

The present invention relates generally to systems for controlling fluid flow, and in particular to medical infusion technology, although other embodiments are possible.

2. Description of Related Art

The precise and accurate regulation of fluid flow is required in many settings. Precision and accuracy are particularly vital in medical infusion rates. For example, in chemotherapy, too slow an infusion rate may prove inefficacious while too rapid a rate may prove toxic to the patient.

However, various elements inherent in medical infusion systems render problematic precise fluid delivery. One factor is the tubing that is used to deliver the fluid. Opening and closing of the line is typically accomplished by clamps, which can distort the walls of the tube leading to irregular flow rates. A second factor is that the patient receiving medication may move during infusion, producing varying fluid column heights, thereby affecting fluid flow. Third, the fact that fluid is delivered from a finite reservoir, such as an intravenous bag or bottle, that gradually empties, also affects the infusion rate.

Numerous approaches are known in the art to compensate for these factors. Certain prior art systems incorporate optical drop counting. Enhanced drop counting systems update drop count data with other measured quantities in order to compensate for varying drop size and splashing. Other approaches include bag weighing and pumping to regulate flow. However, systemic error is inevitable in most, if not all, of these arrangements.

SUMMARY OF THE INVENTION

The present invention provides a system for measuring flow of a fluid through a line. The system isolates a portion of the fluid in the line in a rigid container, so that the fluid in the container is not affected by pressure in the rest of the line. An apparatus is provided for measuring that portion of the container that is not occupied by the fluid. As will be described in detail below (in the SUMMARY OF THE INVENTION and the DESCRIPTION OF SPECIFIC EMBODIMENTS), this volume measurement apparatus uses a measurement gas. If the volume of the container is known, it would then be a simple calculation to determine the volume of the fluid in the container. However, for controlling flow the volume of the container does not need to be known. The system merely measures the unoccupied portion of the embodiment before fluid is dispensed down the line and after fluid is dispensed down the line; the difference between the two volumes is of course, the volume of fluid dispensed. It is important that the container not change volume during the dispensing cycle; hence, a "rigid" container is used.

In order to urge fluid into and out of the container, a positive pressure source, typically greater than ambient pressure, and a negative pressure source, typically less than ambient, are provided for. The positive pressure source provides measurement gas to the container. Thus, the positive pressure can be used to urge fluid out of the container. The negative pressure source removes measurement gas from the container, i.e., applies suction to the container. Thus the negative pressure can be used to urge fluid into the container.

A typical flow cycle using this system would be: first, drawing fluid into the container by using the negative pressure source; then isolating the container so that the measurement apparatus can accurately measure how much of the container is not filled with fluid; after making this measurement, forcing fluid out of the container using the positive pressure source; after dispensing the fluid, re-isolating the container for another measurement of how much of the container is not filled with fluid; and then finally, subtracting the two measurements to determine how much fluid was dispensed. This cycle can be repeated until the desired amount of fluid is dispensed. Alternatively, by measuring how much of the container is not filled with fluid before the fluid is drawn into the container and after fluid is drawn into the container, one can determine, simply by subtracting the two measurements, how much fluid has been drawn into the container. Thus, one can ensure that there is no leak in the container, or other errors, by making sure that the amount of fluid entering the container over a period of several cycles is nearly the same as the amount of fluid exiting the line over the same period.

The measurement apparatus, mentioned above, for measuring how much of the container is not occupied by the fluid, can have a variety of embodiments, all of which use a measurement gas which is permitted to fill the unoccupied portion of the container so that the measurement gas is in fluid communication with the fluid.

One embodiment of the measurement apparatus includes a reservoir for holding a fixed, known volume, Vr, of measurement gas, a valve connecting the reservoir and the container, a pressure transducer for measuring the pressure in the reservoir and a device for changing the pressure in the reservoir.

A second embodiment of the measurement apparatus includes a reservoir for holding a fixed, known volume of measurement gas, a pump connecting the container and the reservoir (instead of a valve and a separate device for changing the pressure in the reservoir), and two pressure transducers, one for the container and one for the reservoir.

A third embodiment changes the volume of the container by a known increment and measures the pressure before and after this change with a transducer for the container.

It will be appreciated that a controller, typically a microprocessor, is used in all the various embodiments of the invention, for reading the pressure measurements and controlling the various valves and pumps used.

BRIEF DESCRIPTION OF THE DRAWINGS

Like reference numerals refer to like items.

DESCRIPTION OF SPECIFIC EMBODIMENTS

Figure 1:
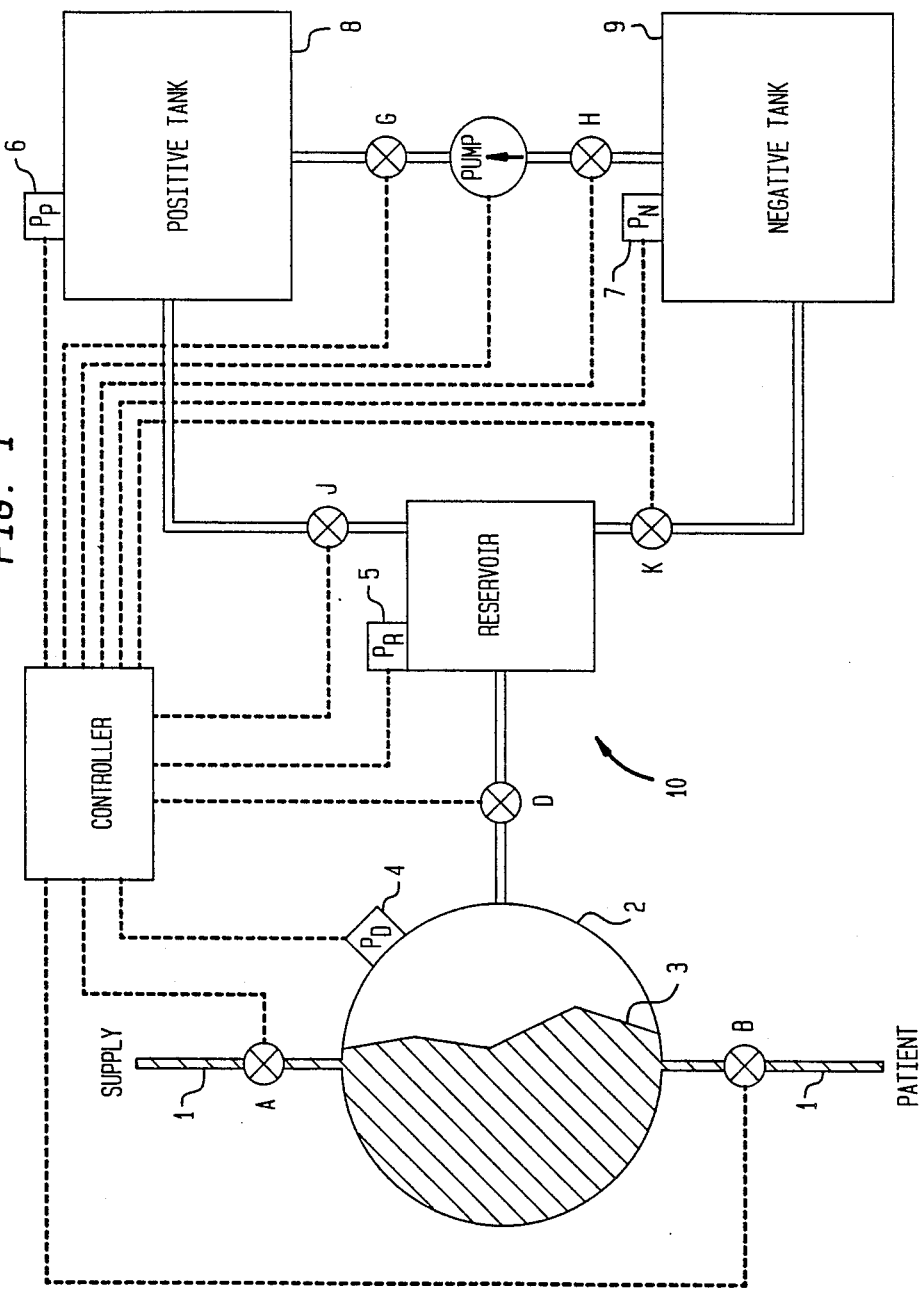
FIG. 1 shows a schematic drawing of a preferred embodiment of the present invention.

FIG. 1 depicts a preferred embodiment of the present invention. A fluid, depicted by the hatching, is in a line 1 which in a typical application is an intravenous line running from a supply, e.g., an intravenous bag, to the patient. Disposed in the line is a rigid container 2, having an input at valve A and an output at valve B. Valves A and B can be closed so that the container 2 is isolated from the effects of pressure in the rest of the line 1. In a preferred embodiment the container 2 is divided by a membrane 3, which separates that portion of the container that is filled with fluid from the remaining portion that is filled with a measurement gas, which is typically air. The membrane 3 is pliable enough so that the pressure of the measurement gas is the same as the pressure of the fluid, and so that the membrane may move as the amount of liquid in the container changes.

For intravenous and other medical applications, the container and valves A and B are preferably built into a disposable cartridge, so that the area of the system that comes in direct contact with the fluid can be removed, disposed, and replaced with another cartridge whenever the system is to be used on a different patient. Putting the container and valves A and B in a disposable cartridge avoids the problems of trying to clean and sterilize those areas of the system that came into contact with the fluid. Because the container is often in a disposable cartridge, it can be referred to as the "disposable".

FIG. 1 shows a pressure transducer 4 for measuring the pressure, Pd, in the container (i.e., the disposable). As will be seen in the cycles below, in many applications a separate pressure transducer 4 is not needed, because the pressure transducer 5 for measuring the pressure, Pr, in the reservoir can measure the pressure of the container when valve D is opened and the reservoir and the container thereby achieve the same pressure. Nevertheless, it is sometimes necessary or preferable to monitor the pressure, Pd, of the container when valve D is closed.

FIG. 1 also shows a reservoir, which is of a constant, known volume. In many of the cycles for measuring or controlling fluid flow through the line 1, the primary purpose of the reservoir is to measure how much of the container 2 is not filled with fluid. (Vu will be used to denote the "unoccupied volume" of the container.) The embodiment shown in FIG. 1 uses the positive tank 8 or the negative tank 9 in addition to the reservoir, to measure Vu.

The positive and negative tanks serve as sources of positive and negative pressure respectively—positive and negative with respect to the pressure in the container. FIG. 1 shows a pump connected to the positive tank 8 by valve G and to the negative tank 9 by valve H. This pump is used to move the measurement gas from the negative tank 9 to the positive tank 8, thereby creating a higher pressure in the positive tank 8 and a lower pressure in the negative tank 9. In order to prevent leakage of measurement gas back from the positive tank to the negative tank, valves G and H are closed when the desired positive and negative pressures are obtained, and the pump is then turned off. Pressure transducers 6 and 7 are used to monitor the pressures in the positive and negative tanks respectively. In the FIG. 1 embodiment the positive and negative pressure supplies (i.e., the positive and negative tanks) can be supplied directly to the reservoir by valves J and K respectively. In order to measure Vu (the volume of the unfilled portion of the container 2) using the embodiment shown in FIG. 1, the following cycle of steps can be performed if the volume of the reservoir Vr is known.

Volume (Vu) Calculation Cycle for FIG. 1 Embodiment

Sept 1—ISOLATE THE CONTAINER: close valves A and B.

Step 2—EQUALIZER PRESSURE IN THE CONTAINER AND THE RESERVOIR: open valve D.

Step 3—MEASURE PRESSURE P1 IN THE CONTAINER: read Pr from transducer 5.

Step 4—ISOLATE THE CONTAINER FROM THE RESERVOIR: close valve D.

Step 5—CHANGE PRESSURE IN RESERVOIR: open valve J to expose the reservoir to the higher pressure from the positive pressure source (or, in the alternative, open valve K to expose the reservoir to the lower pressure from the negative pressure source).

Step 6—MEASURE PRESSURE P2 IN THE RESERVOIR: read Pr from the transducer 5.

Step 7—EQUALIZE PRESSURE IN THE CONTAINER AND THE RESERVOIR: open valve D.

Step 8—MEASURE PRESSURE P3 IN THE CONTAINER: read Pr from transducer 5.

Step 9—CALCULATE Vu: solve $$Vu = -((P3 - P2)Vr)/(P3 - P1),$$

where Vr is the volume of the reservoir.

The equation in step 9 is derived using Boyle's Law for ideal gases. After completing this cycle, the volume of fluid in the container 2 can be determined if the volume of the container 2 is known; merely subtract Vu, the unoccupied volume, from the total volume (occupied and unoccupied) of the container 2.

If a separate pressure transducer 4 is provided for the container 2, one does not have to equalize the pressure between the container 2 and the reservoir, as is done in steps 2 and 7 above, and instead the container 2 and the reservoir can be isolated through all the steps except step 7. Thus, step 2 can be eliminated; the initial pressure in the container, Pd1, is still measured in step 3, but with the transducer 4 for the container 2; step 4 can be dropped since the reservoir and the container are already isolated; step 5 is modified to ensure that the reservoir pressure, Pr1, is different than the container pressure, Pd1; as in the above cycle, step 6 involves measuring the reservoir pressure, Pr1; step 7 can be modified to merely allow some measurement gas to pass between the reservoir and the container, not necessarily until both the container and the reservoir are the same pressure; step 8, is modified to measure the new pressures in the container, Pd2, and the reservoir Pr2; and step 9 uses a different equation:

$$Vu = -((Pr2-Pr1)Vr)/(Pd2-Pd1).$$

This modified cycle is set out below:

Alternative Volume (Vu) Calculation Cycle for FIG. 1 Embodiment

Step 1—ISOLATE THE CONTAINER: close valves A, B, and D.
Step 2—(eliminated)
Step 3—MEASURE PRESSURE Pd1 IN THE CONTAINER: read Pd1 from transducer 4.
Step 4—(eliminated)
Step 5—CHANGE PRESSURE IN RESERVOIR IF SAME AS PRESSURE Pd1 IN CONTAINER: read Pr from transducer 5, and if necessary open either valve J or valve K.
Step 6—MEASURE PRESSURE Pr1 IN THE RESERVOIR: read Pr1 from transducer 5.
Step 7—ALLOW SOME MEASUREMENT GAS TO FLOW BETWEEN THE RESERVOIR AND THE CONTAINER: open and close valve D.
Step 8—MEASURE PRESSURES Pd2 IN THE CONTAINER AND Pr2 IN THE RESERVOIR: read transducers 4 and 5.
Step 9—CALCULATE Vu: solve $$Vu = -((Pr2-Pr1)Vr)/(Pd2-Pd1).$$

This cycle is useful if one does not wish to wait for the pressures in the reservoir and the container to equalize; as may be the case if there is a long thin passage between the two so that it took some period of time after valve D was opened for the pressures to equalize.

Preferably, for both cycles, set forth above, the volume of the reservoir, Vr, is chosen so that it is approximately the same as (or the same order of magnitude as) the volume of the unfilled portion of the container, Vu. This is preferred so that the changes in pressure in both the container and the reservoir are about the same, and thus errors in measuring the pressures or performing the volume calculations are minimized.

On the other hand, the positive tank 8 and the negative tank 9 are preferably much larger than the reservoir and the unfilled portion of the container 2. The reason for this preference is that the pressure in the tanks, Pp and Pn, are preferably kept at desired levels (by monitoring transducers 6 and 7 and activating the pump appropriately), and when either tank is exposed to the reservoir (by opening either valve J or K) the reservoir will pressurize to the pressure level of the tank, and the pressure level of the tank will not change much. Relative to the amount of gas in the tank, a small amount of gas has moved to the reservoir, thus the pressure in the tank is not altered much. This arrangement is desired when there is a desire or need to quickly pressurize the reservoir to a certain pressure, positive or negative.

As noted above, the positive and negative pressure sources (in this embodiment the tanks) can be used to pump fluid through the line by alternatively applying suction and pressure to the membrane 3 of the container 2. A cycle using FIG. 1 embodiment for pumping fluid through the line at a controlled rate is set forth below.

Flow Measurement (Pump) Cycle for FIG. 1 Embodiment

Step 1—INITIALIZE: create positive pressure in positive tank; create negative pressure in negative tank;
Step 2—FILL CONTAINER: close valves B and J; and open valves A, D and K.
Step 3—ISOLATE CONTAINER: close valves A and K.
Step 4—PERFORM VOLUME CALCULATION SUBCYCLE:
  (i) read pressure in the container (by using the pressure transducer 5 for the reservoir. Note: in this cycle the disposable does not need its own pressure transducer. Furthermore, in order to minimize measurement errors, it is preferred to use the same transducer for all pressure measurements.);
  (ii) isolate container from reservoir by closing valve D;
  (iii) change pressure in reservoir by opening and then closing either valve J or K;
  (iv) read pressure in reservoir;
  (v) open container to reservoir by opening valve D;
  (vi) read new pressure in container; and
  (vii) calculate initial volume of fluid in container, if volume of container is known (otherwise, calculate Vu, the unoccupied volume).
Step 5—DELIVER FLUID: open valves B and J. (Note: valve D is open.)
Step 6—ISOLATE CONTAINER: close valves B and J.
Step 7—REPEAT VOLUME CALCULATION SUBCYCLE: perform substeps (i)-(vi) of Step 4; and calculate final volume of fluid in container (or final Vu).
Step 8—CALCULATE VOLUME DELIVERED (in Step 5): subtract the final volume calculated in Step 7 from the initial volume calculated in Step 4 (or subtract the initial Vu from Step 4 from the final Vu from Step 7).

Figure 2:
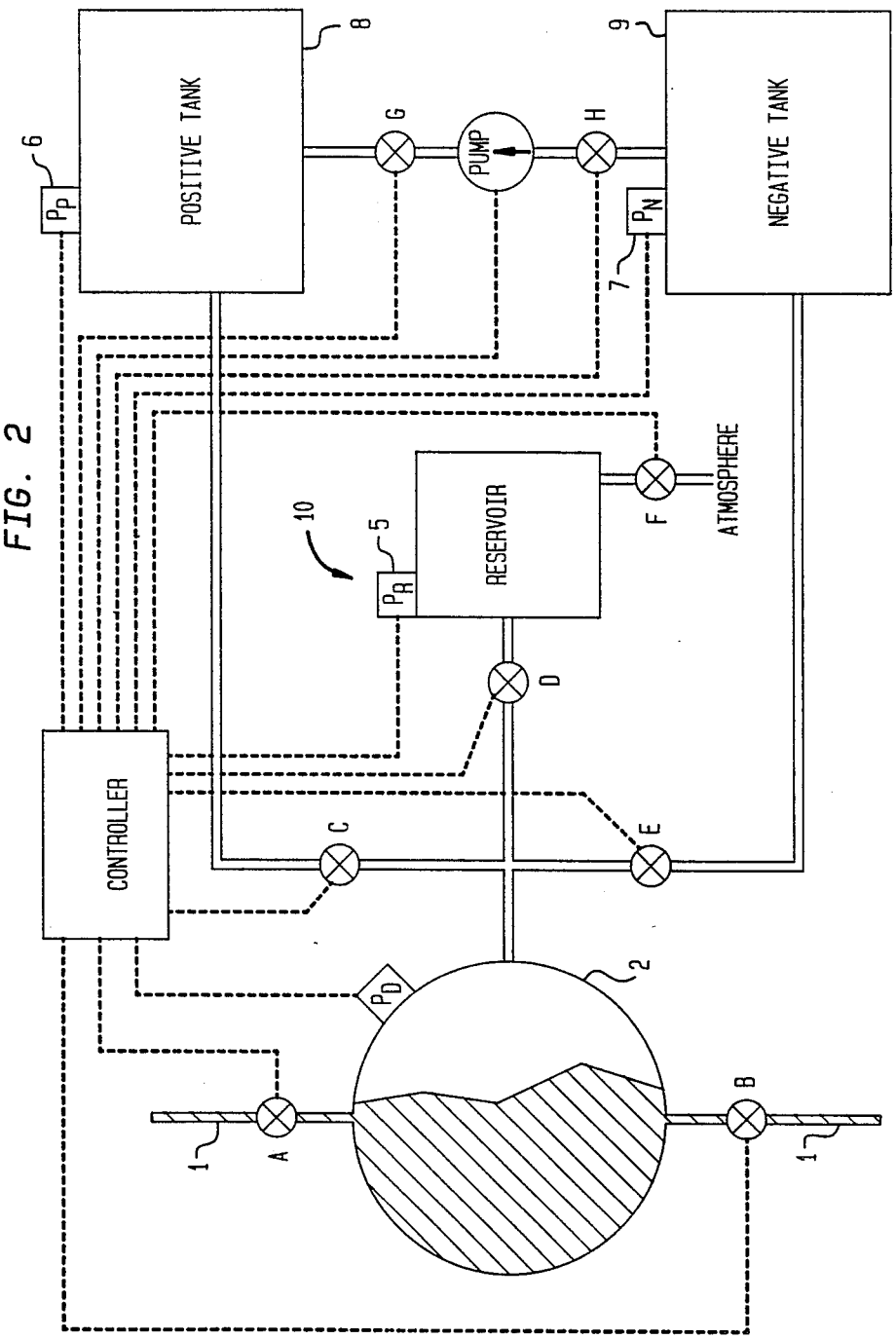
FIG. 2. shows a schematic drawing of an alterative embodiment of the present invention.

FIG. 2 shows an alternative embodiment of the invention. It is very similar to the embodiment depicted in FIG. 1, except the positive and negative pressure sources, 8 and 9, can be applied directly to the container 2 without passing through the reservoir. Also, the reservoir can be vented to ambient pressure by opening valve F. By venting the reservoir, one can change the pressure, Pr, in the reservoir without using the positive and negative pressure sources, 8 and 9. A venting valve could also have been used in the FIG. 1 embodiment.

A cycle for pumping fluid at a controlled rate using the FIG. 2 embodiment is set forth below.

Flow Measurement (Pump) Cycle for FIG. 2 Embodiment

Step 1—INITIALIZE: create positive pressure in positive tank; create negative pressure in negative tank; and close valve F.

Step 2—FILL CONTAINER: close valves B and C; and open valves A and E.

Step 3—ISOLATE CONTAINER: close valves A and E.

Step 4—PERFORM VOLUME CALCULATION SUBCYCLE:
  (i) open valve D;
  (ii) read pressure in the container (by using the pressure transducer 5 for the reservoir. Note: in this cycle the container does not need its own pressure transducer—as noted above, the reservoir pressure transducer can and should be used.);
  (iii) isolate the container from the reservoir by closing valve D;
  (iv) vent the reservoir by opening valve F;
  (v) read pressure in the reservoir (should be equal to ambient pressure);
  (vi) isolate the reservoir by closing valve F;
  (vii) open the container to the reservoir by opening valve D;
  (viii) read new pressure in the container; and
  (ix) calculate initial volume of fluid in the container (or the initial Vu, the volume of the unfilled portion of the container).

Step 5—DELIVER FLUID: open valves B and C.

Step 6—ISOLATE CONTAINER: close valves B and C.

Step 7—REPEAT VOLUME CALCULATION SUBCYCLE: perform substeps (i)–(viii) of Step 4; and calculate final volume of fluid in container (or the final Vu).

Step 8—CALCULATE VOLUME DELIVERED (in Step 5): subtract the final volume calculated in Step 7 from the initial volume calculated in Step 4 (or subtract the initial Vu, calculated in Step 4 from the final Vu calculated in Step 7).

One can see, that the flow measurement (pump) cycles for FIGS. 1 and 2 are very similar. One difference is how the volume, Vu, can be measured—in the FIG. 2 embodiment, the pressure, Pr, in the reservoir is changed by venting the reservoir to the atmosphere.

Figure 3:
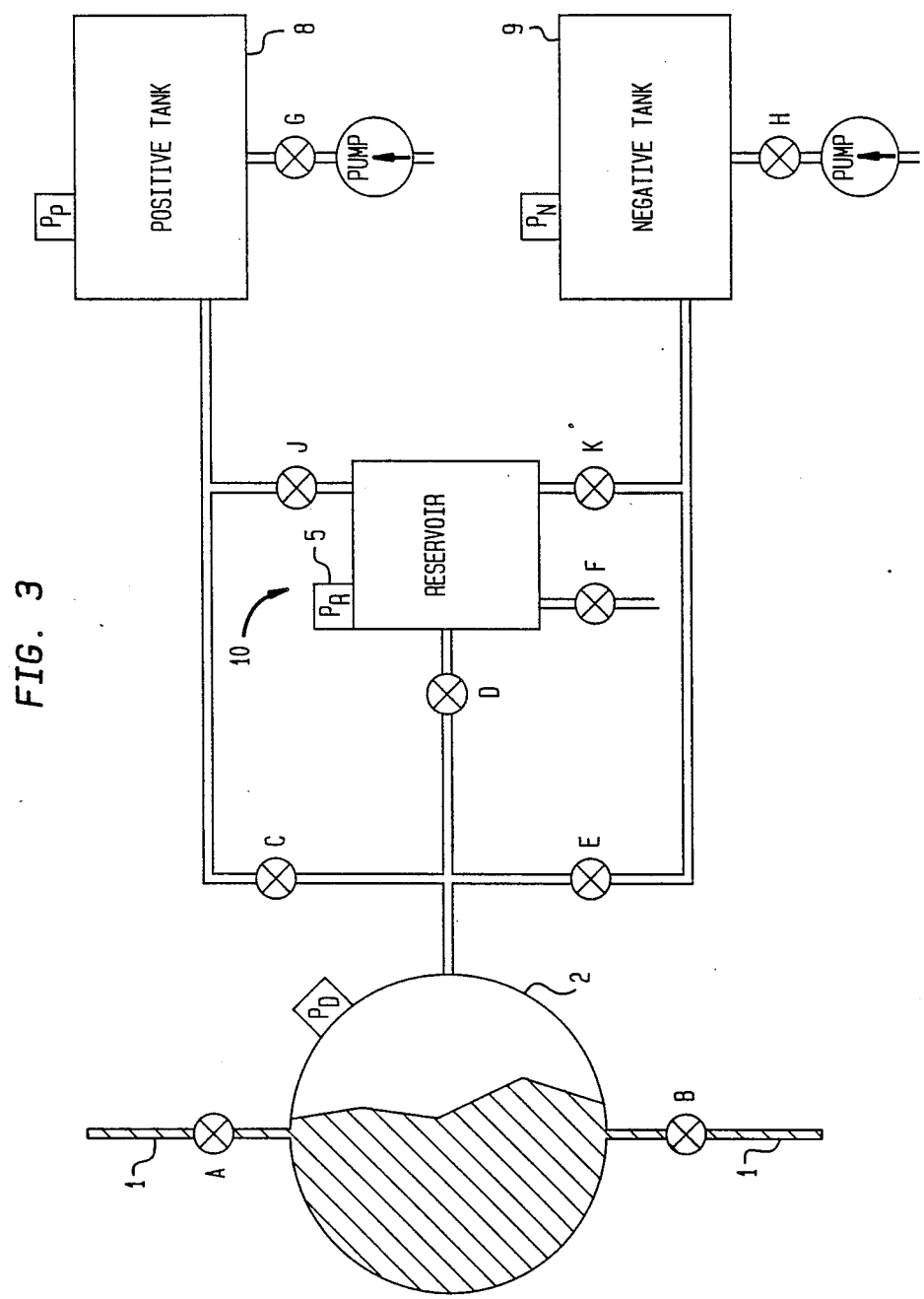
FIG. 3 sows a schematic drawing of a further embodiment of the present invention, combining characteristics of the embodiments shown in FIGS. 1 and 2.

FIG. 3 shows a third embodiment of the invention, combining aspects of the embodiments depicted in FIGS. 1 and 2. The FIG. 3 embodiment also uses two separate pumps for pressurizing the positive and negative tanks, 8 and 9. Thus, in this embodiment the pressure in the two tanks can be controlled separately. It should be noted that the positive and negative pressure supplies do not necessarily need to use tanks, such as tanks 8 and 9, although the use of large tanks is preferred in order to better regulate the positive and negative pressure sources. In any of the foregoing embodiments, positive and negative pressure can be provided by two separate pumps—one pump adding measurement gas to the system, the other sunctioning measurement gas from the system—connected to the container 2 by means of valves C and E, or to the reservoir by valves J and K. Indeed, a single pump that can alternately pump in one direction and then the other can be used to provide both the positive and negative pressure; i.e., a single pump can be used to add and remove measurement gas from the system.

A cycle using the FIG. 3 embodiment for controlling the flow of fluid through the line 1 is set forth below. (Note that this particular cycle does not pump the fluid through the line 1; rather outside forces, such as head pressure or a pump upstream and/or downstream of the container 2, is needed to move the fluid through the line 1. This cycle merely measures the flow rate, and, if the flow rate is too high, the controller can regulate the opening and closing of valves A and B in order to slow the flow rate.)

Flow Measurement (Non-Pump) Cycle for FIG. 3 Embodiment

Step 1—INITIALIZE: close valves C, E, F, J and K.

Step 2—FILL CONTAINER: close valve B; and open valve A. (Note: sufficient pressure above valve A is required to force the fluid into the container in this non-pump cycle.)

Step 3—PERFORM VOLUME CALCULATION SUBCYCLE:
  (i) equalize pressure between container and reservoir by opening valve D;
  (ii) read pressure in the container;
  (iii) isolate the container from the reservoir by closing valve D;
  (iv) change pressure in the reservoir by opening and then closing valve F or valve J or valve K;
  (v) read pressure in the reservoir;
  (vi) equalize pressure between container and reservoir by opening valve D;
  (vii) read new pressure in container; and
  (viii) calculate initial volume of fluid in container (or initial Vu).

Step 5—DELIVER FLUID: open valve B. (Note: sufficient suction below valve B is required to force fluid out of the container in this cycle.)

Step 6—ISOLATE CONTAINER: close valve B.

Step 7—REPEAT VOLUME CALCULATION SUBCYCLE: perform substeps (i)–(vii) of Step 4; and calculate final volume of fluid in container (or final Vu).

Step 8—CALCULATE VOLUME DELIVERED (in Step 5): subtract the final volume calculated in Step 7 from the initial volume calculated in Step 4 (or subtract the initial Vu calculated in Step 4 from the final Vu calculated in Step 7).

As can be seen in substep (iv) of Step 3 in this cycle, and the two alternative volume (Vu) calculation cycles for the FIG. 1 embodiment set forth earlier, the structures shown in FIG. 1-3 can be used in a variety of ways to measure how much of the container 2 is not occupied by fluid (Vu). Other structures can be used to measure Vu. For instance, the measurement apparatus 10 for measuring Vu, of FIG. 2, which includes the reservoir, valves D and F, and the pressure transducer 5, can be replaced with the two alternative measurement apparatus shown in FIGS. 4 and 5. All of the measurement apparatuses discussed herein, including those depicted in FIGS. 4 and 5, use a measurement gas and Boyle's Law for measuring Vu. Other kinds of measurement apparatuses may be available, but it is felt that the ones disclosed herein are more accurate and less expensive.

Figure 4:
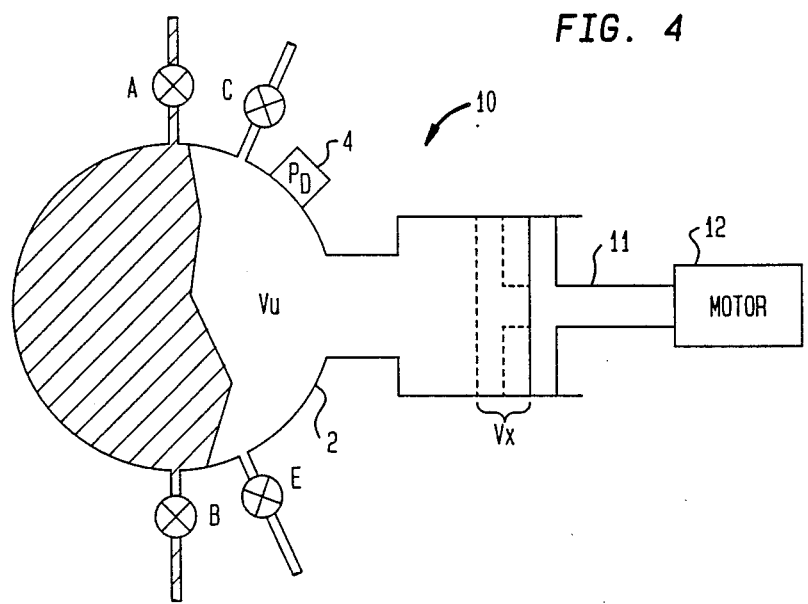
FIG. 4 shows a schematic drawing of a measurement apparatus that can be used in the present invention, instead of the measurement apparatus shown in FIGS. 1–3.

The measurement apparatus 10 shown in FIG. 4 does not have a reservoir that can be isolated from the container. Essentially, the way the FIG. 4 embodiment works is: after isolating the container, the initial pressure, Pd1, of the container is measured; then the volume of the container is changed by a known amount Vx; the final pressure, Pd2 is measured; and Vu is determined by the following equation:

$$Vi = -Pd2(Vx)/(Pd2 - Pd1).$$

The volume is changed by a piston 11 that is moved by a motor 12. The pressure measurements are made by pressure transducer 4. This apparatus is described in greater detail in U.S. Pat. No. 4,808,161 (cross-referenced above) issued to the present inventor. (Note that the lines to the positive and negative pressure sources are connected directly to the body of the container; of course, there is no substantive difference between these connections and the connections to the positive and negative tanks shown in FIGS. 2).

Figure 5:
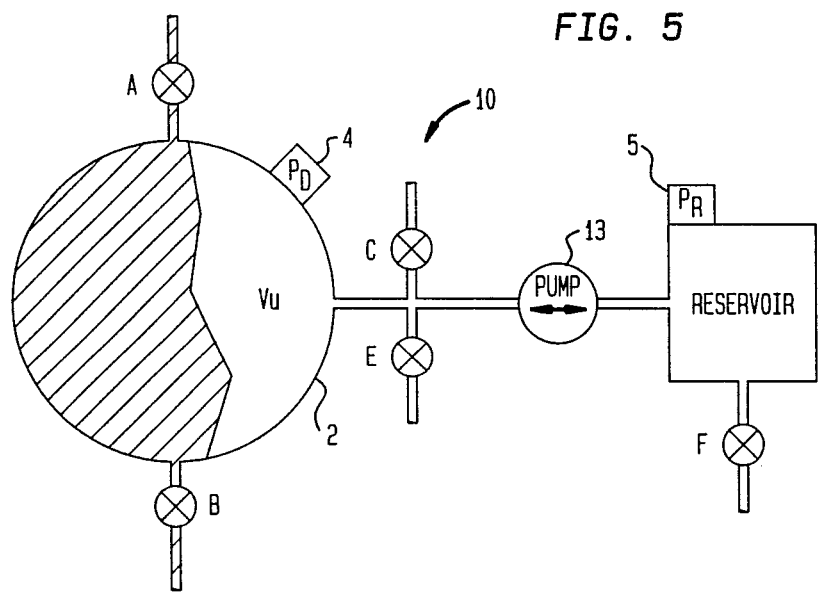
FIG. 5 shows a schematic drawing of another measurement apparatus that can be used in the present invention, instead of the measurement apparatuses shown in FIGS. 1–4.

The measurement apparatus 10 shown in FIG. 5 performs in a manner similar to the measurement apparatus shown in FIGS. 1, 2 and 3; the volume, Vr, of the reservoir must known and fixed, and the pump 13, located where valve D is in FIG. 2, is used both to change the pressure in the reservoir (and the container 2) and to valve measurement gas between the reservoir and the container 2. (If the pump leaks gas when it is off, then of course, a valve, which can be closed to prevent fluid flow between the container 2 and the reservoir, should be placed in series with the pump.) Essentially, the way the FIG. 5 embodiment works is: after isolating the container 2 and the reservoir, the pressure in each is measured, Pd1 and Pr1; then, some measurement gas is pumped from the container to the reservoir or vice-versa; the new pressures in the container and the reservoir are measured, Pd2 and Pr2, and the volume, Vu, of the unfilled portion of the container is determined by the equation:

$$Vu = -((Pr2 - Pr1)Vr)/(Pd2 - Pd1)$$

One will note that two separate transducers, 4 and 5, are needed to measure the pressures in the container and the reservoir. Also, a valve F has been included in this embodiment, although not absolutely necessary, so that one may vent the reservoir to atmosphere between cycles. This apparatus is described in greater detail in co-pending application Ser. No. 092,481 (cross-referenced above, and a continuation-in-part of U.S. Pat. No. 4,808,161) issued to the present inventor.

One can see how the apparatus in FIGS. 4 and 5, can be used to suction fluid into the container 2 or force fluid out of the container independently of the positive and negative pressure sources—the FIG. 4 embodiment can use its motor-driven piston 11, and the FIG. 5 embodiment can use its pump 13.

A special valve system has been designed for use with the disposable cartridge embodiment above. Specifically, this valve system can be used for valves A and B in the above embodiments, since these valves come in contact with intravenous fluid and therefore should be part of the disposable cartridge. The valve system is characterized by the use of a second control fluid, such as air. (The control fluid can be different than the measurement gas, but preferably both are air.) This control fluid urges a flexible membrane against a receiving surface such that a seal is formed and the line is closed off. The fluid line, flexible membrane, and receiving surface are arranged in such a mechanically advantageous manner that relatively little fluid pressure in the control line is required to close off fluid under relatively high pressure in the main line.

Figure 6A:
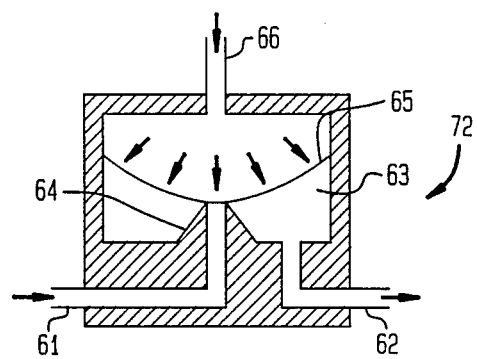
FIGS. 6A and 6B show two types of valves that can be used in the present invention.

One simple embodiment of the present invention is shown in FIG. 6A, wherein a single valve is provided. The fluid line input 61 and output 62 are mounted to a fluid tight valving chamber 63. It is contemplated that this valving chamber 63 be made of a rigid material, such as molded hard plastic. The valving chamber includes fittings for the input and output lines. The valving chamber further includes a mouth 64 connected to the fluid input 61, which in the present embodiment displays a beveled contour to facilitate efficient sealing. However, it would also be possible within the spirit of the invention to have a mouth 64 that is flush with the wall of the chamber.

One wall of the valving chamber is provided with a flexible impermeable membrane 65, which is in communication with a control fluid supply line 66. The membrane 65 is mounted with relation to the control fluid supply line 66 and the mouth 64 such that when control fluid pressure is increased in the control fluid supply line 66, the flexible membrane 65 is urged against the mouth 64. A material is chosen for the membrane 65 such that the membrane "grips" the mouth 64, thereby enhancing the seal. When it is desired to open the fluid line, control fluid pressure is diminished until main line fluid pressure sufficient to push the membrane 65 away from the mouth, thus break the seal.

Figure 6B:
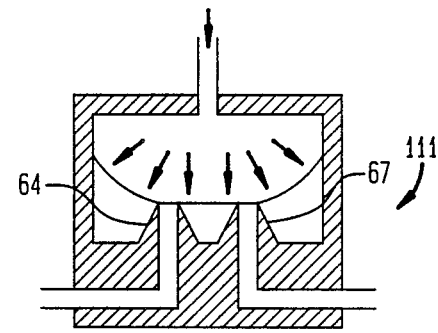

The present embodiment of the invention incorporates mechanical advantage. The control fluid tends to distribute force all along the surface of the membrane. Because of its small diameter the fluid in the fluid input 61 only acts on a small area of the membrane 65. Thus, the control fluid line pressure can produce more force on the membrane than the fluid input pressure (force is equal to pressure times area). FIG. 6B shows another embodiment of this valve, wherein two beveled mouths are used—one for the input 64, one for the output 67. This embodiment is useful if the output fluid may be highly pressurized.

It is contemplated that pressure in the control fluid line could be controlled using a stepper motor employing a cam-actuated piston or other means known in the art. In a piston-based embodiment, a piston would be used to compress the air in the line, thereby increasing the control fluid pressure and closing the valve. The piston would then be retracted to decrease the control fluid pressure and open the valve.

In an alternative embodiment, air would serve as the control fluid. Air could then be stored in an airtight reservoir in communication with the fluid line. A compressor could be used to increase the air pressure in the line, and a solenoid-operated valve would be used to open a communication pathway between the reservoir and the control line, thereby increasing the pressure in the control line. (The foregoing can be controlled by a microprocessor.) When the valve is to be opened, the communication pathway would be closed, and the control line vented to ambient atmosphere. Alternatively, the reservoir could be pressurized using a hand pump.

Regardless of the specific embodiment for the control fluid pressure generating means, it will be seen that the present invention provides numerous advantages. Primary among these advantages is the combination of mechanical reliability with low cost and ease of manufacture.

The valving systems of FIGS. 6A and 6B is mechanically reliable because it has relatively few moving parts. The valving chamber is fixed, as are the line fluid input, line fluid output, and the control fluid line. The only moving parts are the control fluid pressure generating means and the flexible membrane. As discussed above, the control fluid pressure generating means can be implemented using a stepper motor and piston. Piston assemblies, because of the limited range of motion involved, are also mechanically reliable. As further discussed above, the control fluid pressure generating means can also be implemented using a pressurized air reservoir. The only moving parts in such an embodiment would be the valve connecting the reservoir to the control fluid line, and the means used to pressurize the reservoir; furthermore, such a pressurized reservoir may be available in the fluid control system, such as the positive tanks 8 in the systems depicted in FIGS. 1–3. (The negative tanks 9 could be used to pull the membrane 65 from the mouths.)

Further, the flexible membrane can be made of any of a number of readily available, inexpensive materials, for example, the flexible plastic used to make intravenous bags. This material is known to be extremely rugged, in addition to being relatively inexpensive. Further, this plastic has excellent "gripping" properties.

Another advantage to using a membrane-based system is that there are none of the known disadvantage inherent in valving systems based on squeezing an intravenous tube. The first disadvantage in a squeezing systems is that it is relatively difficult to obtain a perfect closing of the line. A relatively large amount of energy must be expended to pinch an intravenous line closed, because of the difficulty in "folding" the edges of a pinched tube. A further disadvantage is cold flow. An intravenous tube will, after repeated openings and closings, tend to change shape around the pinching site. This in turn decreases the mechanical reliability of the intravenous delivery system. None of these disadvantages are present in a membrane-based system. As discussed above, because of the mechanical advantage inherent in this system, relatively little energy is required to close the valve. And because there is no pinching involved, cold flow does not present a significant problem.

Further, the device does not require precision molding. The valve will tolerate a broad range of manufacturing imperfections. For example, even if the valve chamber mouth is not perfectly aligned, the membrane will still seal against it. Even if the control fluid line is slightly off center, the membrane will still be urged against the valve chamber mouth. The only stringent requirements are that the valve chamber, including input and output lines, be fluidtight, and that the control fluid line be airtight.

In addition, the utility of this valving system can be enhanced by the manufacturing method used. For example, it would be possible to construct the input line, valving chamber (including mouth), output line and membrane all into a single disposable unit that could also include the container 2 (more precisely half the container—the half that is filled with liquid) shown in FIGS. 1–5. The membrane would be attached to a rigid plastic structure that could be sized to fit snugly onto a central flow control system unit. Any of the various flow control systems discussed hereinabove could be adapted to work with a disposable.

In one embodiment of a flow control system, it is contemplated to mold the portion of the pressure/volume measurement housing containing intravenous fluid (the left half of container 2 in FIGS. 1–5) together with input and output pathways and membrane-based valving chambers all out of the same block of plastic. The same sheet of membrane can be used as the membrane 65 in the valves and as the interface (See item 3 in FIG. 1) between the intravenous fluid and the measurement gas. Two such housing units are depicted in FIGS. 7–9 and FIG. 11.

Figure 7:
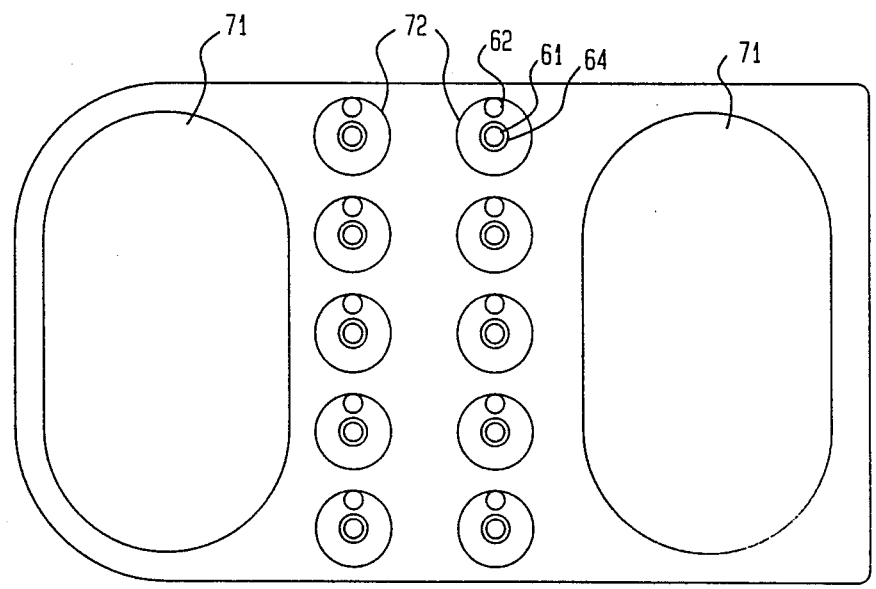
FIG. 7 shows cross-sectional views of a disposable cartridge, or cassette, that can be used in the present invention.
Figure 9:
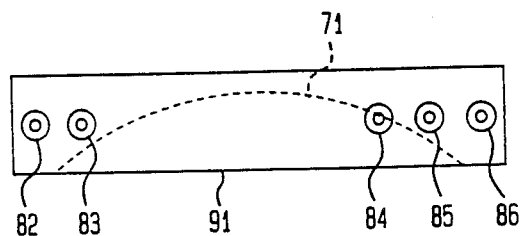
FIG. 9 shows an end view of the disposable cassette of FIG. 7.
Figure 8:
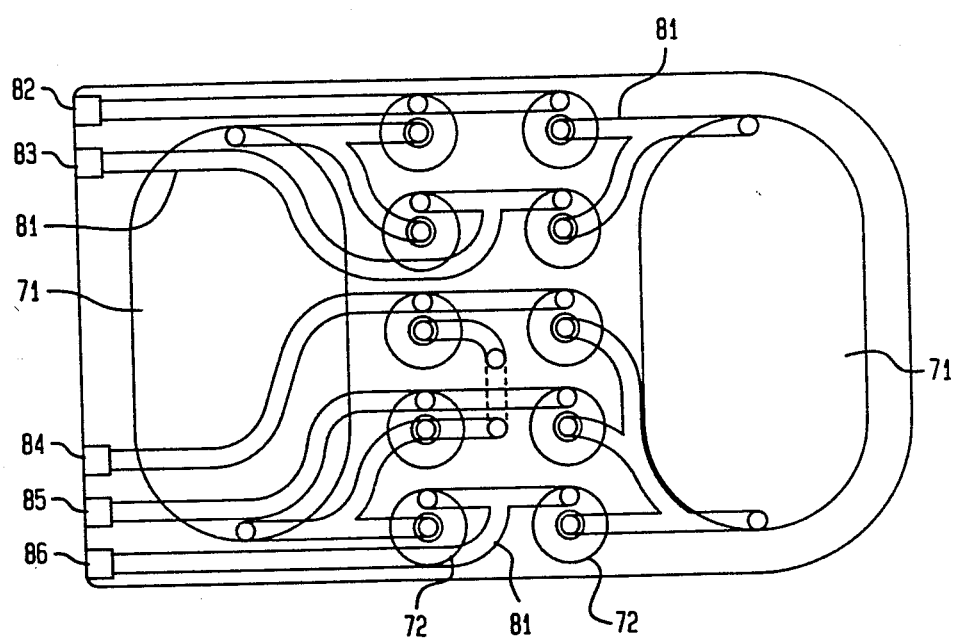
FIG. 8 shows a bottom view of the disposable cassette of FIG. 7 and its internal piping.
Figure 10:
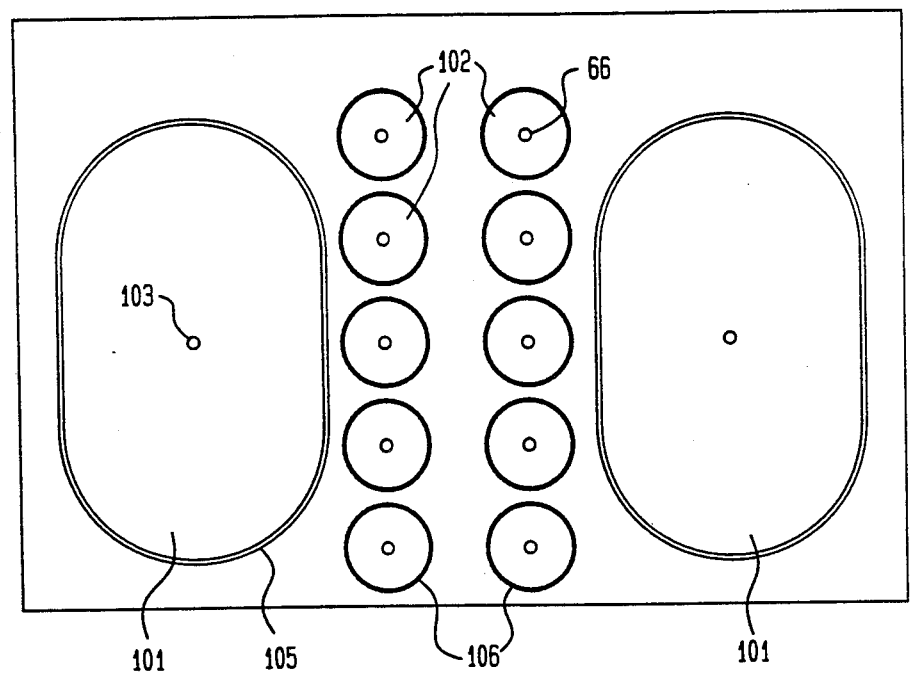
FIG. 10 shows a plan view of the face of the central system unit against which the disposable cassette of FIG. 7 is placed against.

The housing unit would be affixed to a receiving block, such as that shown in FIG. 10, which would be used with the housing unit depicted in FIGS. 7–9. The housing unit could be held in place by a retaining clamp, or by other means known in the art. Sealing rings are provided to insure that the control fluid pathways, and the measurement gas pathways remain fluidtight. In this embodiment, it is contemplated that the housing unit would be disposable, and that the receiving block would be an integral part of the central flow control system unit. It will be seen that this is a desirable arrangement. The housing unit is used to transport intravenous fluid, and must therefore be sterile. It would be impractical to clean and sterilize such a unit for multiple uses. The receiving block, on the other hand, must be sturdy, to insure a proper seal, and to insure proper operation of the valves.

It is contemplated that the controller (i.e., the microprocessor) could be programmed to perform a safety protocol during calibration of the device to check that all the seals are tight. During such a protocol, control fluid pressure to various valving chambers would be manipulated, and the resulting pressure changes would be monitored using the pressure transducers already present in the system. Aberrant conditions would cause an alarm state to be entered into.

Not all pathways would be required for all applications of the controller unit. It would be possible to design and manufacture a "universal" housing unit that would embody all possible pathway configurations for various situations. The receiving block could then be adapted for specific controller applications. Alternatively, the microprocessor could be programmed to valve off pathways, as required.

FIG. 7 shows one embodiment of a disposable housing unit (or "cartridge" or "cassette"). This particular unit has two concave indentations 71 for the container portion of the disposable, so that two fluid control systems can function in parallel. In a preferred embodiment, two fluid control systems are used to deliver intravenous fluid to a patient in order to make the flow of fluid smoother. As one container 71 is dispensing, the other is filling. Thus, fluid is delivered in more closely spaced and smaller pulses, rather than larger pulses that come less frequently and that have longer periods between them.

The disposable cartridge shown in FIG. 7 also has ten valves 72 of the type depicted in FIG. 6A, with the input 61 and the output 62 showing. This side of the unit has a membrane stretched across and attached to it that serves as the membrane (65 in FIG. 6A) for the valves 72 and the membrane (3 in FIG. 1) for the container 71. (See item 91 in FIG. 9.)

FIG. 8 shows a bottom view of the disposable cartridge showing the internal piping or passageways 81, which are inside the disposable cartridge and which connect the various valves 72, the container indentations 71 and the various inputs and outputs 82–86. The inputs and outputs can be arranged in a variety of ways; for example, the top two ports 82 and 83 could both be inputs (i.e, valve A in FIGS. 1–5) coming from two different fluid supplies, the bottom two ports 85 and 86 could be outputs (i.e., valve B in FIGS. 1–5). Port 84 could be used to remove samples of the fluid from the container for testing or analyzing. FIG. 9 shows an end view of these ports 82–86, as well as the fluid side of the containers 71 in phantom. The membrane 91 for the valves 72 and the containers 71 is attached to the disposable cartridge on the side indicated (91). The membrane 91 billows in and out depending on how much fluid is in the container.

FIG. 10 shows the face of the flow control system unit, against which the disposable shown in FIGS. 7–9 is placed and held by a clamping device. There are two large indentations 101 on the system unit to match the indentations 71 on the disposable. These indentations 101 on the system unit are basically the measurement gas portion of the container. Each indentation has an aperture 103, through which measurement gas passes. As discussed extensively above, the measurement gas is used to measure how much of the complete container is not occupied by the fluid (when the container is isolated), to suction fluid into the container, and to force fluid out of the container.

FIG. 10 also shows receptacles 102 for the valves 72 and an aperture 66, through which the valve control fluid passes. The container indentations 101 and the valve receptacles 102 are surrounded by seals, 105 and 106 respectively, so that when the disposable is clamped against the system unit an air-tight seal is formed.

Figure 11:
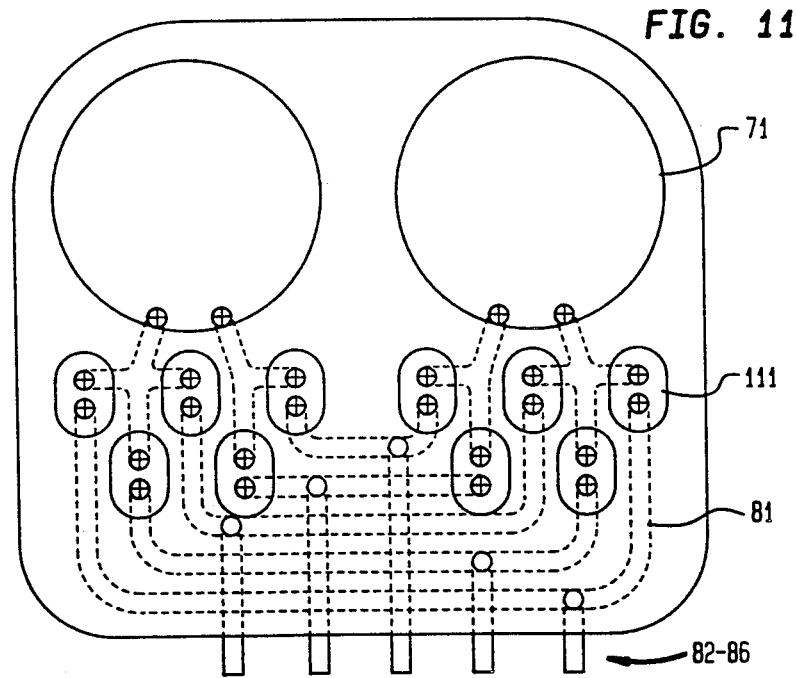
FIG. 11 shows a top plan view of an alternative disposable and its internal piping.

FIG. 11 shows an alternative disposable housing unit that like the disposable housing unit in FIGS. 7–9 has container indentations 71, fluid pathways 81 and input/output ports 82–86. The FIG. 11 disposable, however, uses the valves 111 shown in FIG. 6B. Despite this difference and the different piping layout, the FIG. 11 disposable functions the same way as the disposable in FIGS. 7–9.

Figure 12:
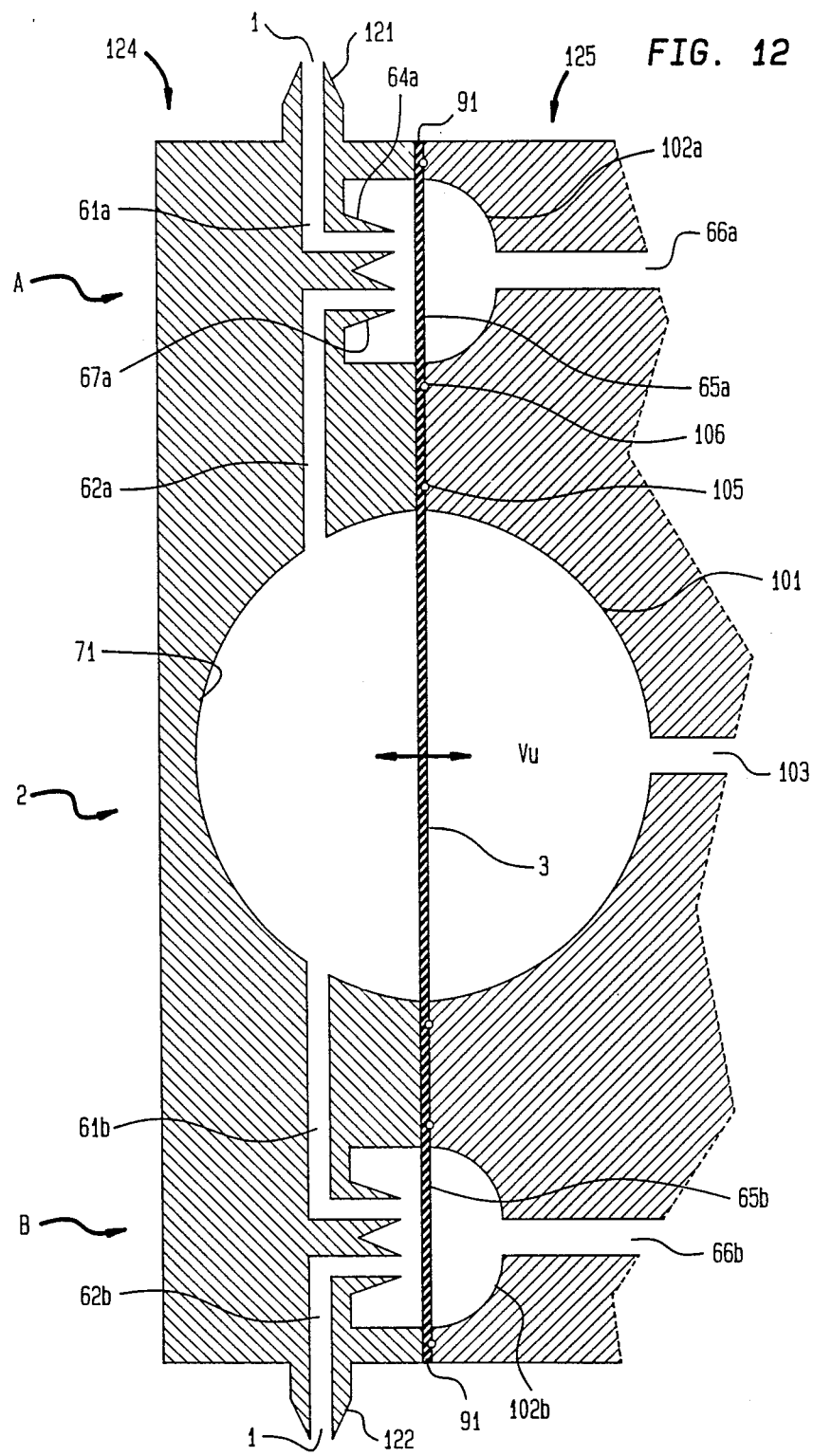
FIG. 12 shows a cross-section of another alternative disposable in contact with the central unit.

FIG. 12 shows a simple embodiment of the disposable housing unit 124 clamped against the face of the central flow control unit 125 designed for this disposable 124. This disposable 124 has only one container 2 and two valves, A and B, and therefore can be used with any of the embodiments depicted in FIGS. 1–5. The input 61a of valve A is connected to the intravenous line 1 by a protrusion 121, which can be inserted in the intravenous tubing. Valve A and valve B are of the type depicted in FIG. 5B; the two beveled mouths 64a and 67a can be seen in valve A. The output 62a of valve A leads in to the left half of the container 2, which is formed by the indentation 71 in the disposable 124. Membrane sheet 91 is attached to the disposable 124 and covers the whole side of the disposable. Parts of this membrane sheet 91 function as the membrane 65a for valve A, the membrane 3 in the container 2, and the membrane 65b in valve B. Valve A is disposed against a receptacle 102a in the central unit 125, which is connected to an air supply 66a through which air is pumped back and forth, thereby effecting the opening and closing of valve A by pulling the membrane 65a back from the mouths 64a and 67a and pushing the membrane 65a against mouths 64a and 67a. In this case, the air is functioning as the valve control fluid.

Channel 103 provides a path for the measurement gas (which can be air) from the container 2 to the rest of the system (including, for example, the reservoir). The membrane 3, which as noted above is part of the flexible sheet 91, moves back and forth depending on how much fluid is in the container 2. If the container has its own pressure transducer (such as item 4 in FIG. 1), this transducer can be placed in fluid communication with the container 2 through channel 103.

The container 2 is connected to the input 61b of valve B, which is disposed against the receptacle 102b and which functions the same way as valve A by means of air supply 66b. The output 62b flows into the intravenous line 1 connected to the patient. A protusion 122 is used to attach the tube to the disposable 124.

In order to ensure the proper sealing between the elements of the disposable, gasket-like seals, 105 and 106, are disposed around the container and the valves.

What is claimed is:

1. A system for measuring in an isolated rigid container partially filled with a fluid, the volume, Vu of that portion of the container that is not occupied by the fluid, such portion being called the unoccupied portion, the system comprising:
    reservoir means for holding a fixed, known volume, Vr, of a measurement gas;
    pressure means for (i) permitting the measurement gas to fill the unoccupied portion of the container, so that the measurement gas is in fluid communication with the fluid in the container, (ii) in a first valve position, permitting the measurement gas to flow between the container and the reservoir means, and, in a second valve position, preventing the measurement gas from flowing between the container and the reservoir means, and (iii) upon activation, changing the pressure in the reservoir means by changing the amount of measurement gas in the reservoir means;
    transducer means for measuring the pressure in the reservoir means; and
    control means for (i) reading pressure measurements from the transducer means, (ii) putting the pressure means into the first or second valve position (iii) activating the pressure means to change the pressure in the reservoir means, and (iv) calculating, based on the pressure measurements and the volume, Vr, of the reservoir means, the volume, Vu, of that portion of the partially filled container that is not occupied by the liquid.

2. A device accordrng to claim 1, further including container transducer means for measuring the pressure in the container; and wherein
    the pressure means includes pump means for, upon activation, moving the measurement gas between the reservoir means and the container; and
    the control means includes means for activating the pump means, and reading pressure measurements from the container transducer means.

3. A device according to claim 1, wherein the pressure means includes a valve that (i) is disposed between the container and the reservoir means,(ii) is open when the pressure means is in a first valve position, and closed when the pressure means is in a second valve position; and the control means includes means for opening and closing the valve.

4. A device according to claim 3, wherein the pressure means includes vent means for, in a first vent position, exposing the reservoir means to the ambient pressure, and, in a second vent position, for isolating the reservoir means from the ambient pressure; and the control means includes means for putting the vent means into the first or second vent position.

5. A device according to claim 3, wherein the control means includes means for performing the following cycle of steps:

opening the valve of the pressure means;
reading the pressure, P1, of the reservoir means;
closing the valve of the pressure means;
activating the pressure means to change the pressure in the reservoir means;
reading the pressure, P2, of the reservoir means;
opening the valve of the pressure means;
reading the pressure, P3, of the reservoir means; and
calculating Vu by solving:

$$Vu = -((P3-P1)Vr)/(P3-P2).$$

6. A system for controlling flow of a fluid through a line, the system comprising:

isolation means for (i) holding a region of the fluid in the line in a rigid container, the rigid container having a larger volume than the region of fluid, and (ii) in a first flow position, permitting fluid to flow into or out of the container and, in a second flow position, isolating the region of the fluid in the line from effects of pressure in the line outside the region;

measurement means for measuring, with a measurement gas in fluid communication with the fluid in the region, the volume Vu, of that portion of the container not occupied by the fluid;

positive pressure means for, upon activation, supplying measurement gas to the isolation means;

negative pressure means for, upon activation, removing measurement gas from the isolation means;

control means for (i) putting the isolation means into the first or second flow position, (ii) activating the positive pressure means and the negative pressure means, and (iii) controlling the measurement means.

7. A system according to claim 6, wherein the measurement means includes:

reservoir means for holding a fixed, known volume, Vr, of the measurement gas;

valve means for, in a first valve position, permitting the measurement gas to flow between the isolation means and the reservoir means, and, in a second valve position, preventing the measurement gas from flowing between the isolation means and the reservoir means;

pressure means for, upon activation, changing the pressure in the reservoir means by changing the amount of measurement gas in the reservoir means; and transducer means for measuring the pressure in the reservoir means; and wherein the control means includes means for receiving pressure measurements from the transducer means, putting the valve means in to the first or second valve position, activating the pressure means, and calculating Vu based on the pressure measurements and the volume, Vr, of the reservoir means.

8. A system according to claim 6, wherein the isolation means includes an input valve for permitting, fluid to flow into the isolation means and an output valve for permitting fluid to flow out of the isolation means and wherein the control means includes means for performing the following cycle of steps:

closing the output valve;
opening the input valve;
activating and de-activating the negative pressure means;
closing the input valve;
activating the measurement means to determine the initial volume, Vu1, of that portion of the container not occupied by fluid;
opening the output valve;
activating and de-activating the positive pressure means;
closing the output valve;
activating the measurement means to determine the final volume, Vu2, of that portion of the container not occupied by fluid; and
subtracting Vu2 from Vu1 to determine the amount of fluid that left the isolation means while the output valve was open.

* * * * *